US005656587A

United States Patent [19]
Sporn et al.

[11] Patent Number: 5,656,587
[45] Date of Patent: Aug. 12, 1997

[54] PROMOTION OF CELL PROLIFERATION BY USE OF TRANSFORMING GROWTH FACTOR BETA (TGF-β)

[75] Inventors: Michael B. Sporn; Anita B. Roberts, both of Bethesda, Md.

[73] Assignee: The United States of America as represented by the Secretary of the Department of Health and Human Services, Washington, D.C.

[21] Appl. No.: 48,956

[22] Filed: Apr. 16, 1993

Related U.S. Application Data

[60] Continuation of Ser. No. 816,563, Jan. 3, 1992, which is a division of Ser. No. 308,948, Feb. 8, 1989, Pat. No. 5,104,977, which is a continuation of Ser. No. 581,021, Feb. 16, 1984, abandoned, which is a division of Ser. No. 500,833, Jun. 3, 1984, abandoned, which is a continuation-in-part of Ser. No. 468,590, Feb. 22, 1983, abandoned, which is a continuation-in-part of Ser. No. 423,203, Sep. 24, 1982, abandoned.

[51] Int. Cl.$^6$ .................. A61K 38/18; C07K 14/495
[52] U.S. Cl. .................. 514/2; 530/399; 514/12; 514/21; 424/85.1
[58] Field of Search .................. 424/86.1; 514/2, 514/8, 12, 21; 530/399

[56] References Cited

U.S. PATENT DOCUMENTS

| | | | |
|---|---|---|---|
| 3,409,605 | 11/1968 | Florini . | |
| 3,699,222 | 10/1972 | Isaacs et al. | 424/85.4 |
| 4,054,557 | 10/1977 | Sievertsson et al. | 530/300 |
| 4,341,765 | 7/1982 | Ruhenstroth-Bauer et al. | 424/101 |
| 4,350,687 | 9/1982 | Lipton et al. | 530/300 |
| 4,479,896 | 10/1984 | Antoniades | 530/380 |
| 4,686,283 | 8/1987 | Nestor, Jr. et al. | 530/327 |
| 4,708,948 | 11/1987 | Iwata et al. | 514/2 |
| 4,742,002 | 5/1988 | Guadagno | 435/28 |
| 4,742,003 | 5/1988 | Derynck et al. | 435/69.4 |
| 4,774,322 | 9/1988 | Seyedin et al. | 530/353 |
| 4,816,442 | 3/1989 | McPherson et al. | 514/14 |
| 4,816,561 | 3/1989 | Todaro | 530/324 |
| 4,843,063 | 6/1989 | Seyedin et al. | 514/2 |
| 5,104,977 | 4/1992 | Sporn et al. | 530/399 |

FOREIGN PATENT DOCUMENTS

| | | |
|---|---|---|
| 184014 | 6/1986 | European Pat. Off. . |
| 128849 | 5/1992 | European Pat. Off. . |
| 2146335 | 4/1985 | United Kingdom . |
| 84-01106 | 3/1984 | WIPO . |

OTHER PUBLICATIONS

Carraco et al, Surgical Clinics of North America, vol. 64(4) 1984, pp. 721–733.
Abstracts of the 20th Annual Meeting on Wound Repair J. Cellular Biochem, Suppl 15F, 1991, pp. 159–169 (varies).
Frolik et al, Proceedings of the First International Syposium, Hearn et al. ed., pp. 1 and 95–101 (Jan. 28, 1983).Frolik et al, Proceedings of the First International Syposium, Hearn et al, ed., pp. 1 and 95–101 (Jan. 28, 1983).
Federation Proceedings, Abstracts, American Society of Biological Chemists, St. Louis, Missouri, May 31–Jun. 4, 1981, Peptides and Peptide Synthesis, p. 1643.
George J. Todaro, Journal of Supramolecular Structure and Cellular Biochemistry 15:287–301 (1981).
Anzano et al, Analytical Biochemistry, 125, pp. 217–224 (1982).
Brown et al, PNAS USA, 84, pp. 3743–3747 (1987).
DeLarco et al, PNAS USA, 75, No. 8, pp. 4001–4005 (1978).
DeLarco et al, Nature, vol. 272, pp. 356–358 (1978).
Holley et al, PNAS USA, vol. 77, No. 10, pp. 5989–5992 (1980).
Massaque et al, J. of Biol. Chem., vol. 260, pp. 4551–4554 (1985).
Marquardt et al, J. of Biol. Chem., vol. 255, No. 19, pp. 9177–9181 (1980).
Marquardt et al, J. of Biol. Chem., vol. 256, No. 13, pp. 6859–6862 (1981).
Moses et al, Oncogenes and Growth Control, Edited by P. Kahn and T. Graf, pp. 50–56 (1986).
Moses et al, Cancer Research, vol. 41, pp. 2842–2848 (1981).
Todaro et al, Cancer Research, vol. 38, pp. 4147–4154 (1978).
Tucker et al, Cancer Research, vol. 43, pp. 1581–1586 (1983).
Todaro et al, PNAS, vol. 77, pp. 5258–5262 (1980).
Roberts et al, PNAS, vol. 77, pp. 3494–3498 (1980).
Kovacina et al, Biochemical and Biophysical Research Communications, vol. 160, No. 1, pp. 393–403 (1989).
Variables in the High–Pressure Cation–Exchange Chromatography of Proteins, Charles A. Frolik, Analytical Biochemistry 125, 203–209 (1982).
High–Performance Liquid Chromatography of Proteins and Peptides, Proceedings of the First International Symposium, Milton T.W. Hearn, Academic Press.
Federation Proceedings, Abstracts 3478–6993, 66th Annual Meeting, Mar. 5, 1982, vol. 41, No. 4.
Anzano et al, Federation Proceedings, vol. 40, No. 6, p. 1643, Abstract No. 598 (May 1, 1981).
Sporn et al, Federation Proceedings, vol. 41, No. 5, Abstract No. 1288 (Mar. 5, 1982).
Roberts et al, PNAS USA, 78, No. 9, pp. 5339–5343 (Sep. 1981).
Frolik et al, Analytical Biochemistry, 125:203–209 (1982).
Todaro et al, Journal of Supramolecular Structure and Cellular Biochemistry, 15:287–301 (1981).

(List continued on next page.)

Primary Examiner—Vasu S. Jagannathan
Assistant Examiner—Christine Saoud
Attorney, Agent, or Firm—Birch, Stewart, Kolasch & Birch, LLP

[57] ABSTRACT

A composition for the promotion of cell proliferation and tissue repair in animals having as active ingredients a TGF-β which is activated by either a TGF-α or an EGF or both; and methods for administration. As another embodiment these active ingredients can be admixed with other (secondary) growth factors.

6 Claims, No Drawings

OTHER PUBLICATIONS

Anzano et al, Proc. of the First Intl. Symp. on HPLC of Proteins and Peptides, Washington, D.C., Nov. 16–17, 1981, Abstract No. 505.
Childs et al, PNAS USA, 79:5312–5316 (Sep. 1982).
Roberts et al, Nature, 295:417–419, Macmillan Journals Ltd., U.S. (1982).
Anzano et al, Cancer Research, 42(11), 4776–8 (1982).
Assoian et al, Federation Proceedings (USA), 42 (7)1831 Abs. 428 (1983).
Frolik et al., PNAS, 80(12):3676–3680 (1983).
Assoian et al, J. Biol. Chem., 258(11):7155–7160 (1983).
Roberts et al, Federation Proceedings, 42(7):1832, Abs. 439 (1983).
Noe et al, Hormone Metab. Res., 7:314–22 (1975).
Permutt et al, J. Clin. Endocrin. Metab., 44:536–44 (1977).
Sporn et al, Science, 219:1329–31 (1983).
American Society of Biological Chemists, 74th Annual Meeting, Abstract Nos. 419, 420, 428, 439, 440 and 853, San Francisco, CA (Jun. 5–9, 1983).
Anzano et al, Proceedings of the First International Symposium, Hearn et al, ed., pp. 111–118 (Jan. 28, 1983).
Anzano et al, International Symposium HPLC Protein Peptide, #505, p. 25 (1981).
Brewer et al, Experimental Techniques in Biochemistry, P. 52 (1974).
Childs et al, Chemical Abstracts 97:142402j (1982).
De Larco et al, Journal of Cellular Physiology, 109:143–152 (1981).
Dicker et al, Chemical Abstracts, 95:201393r (1981).
Frolik et al, Biological Abstracts, 25:45382 (1983).
Massague, The Journal of Biological Chemistry, vol. 258, No. 22, pp. 13614–13620 (1983).
Moses et al, Cancer Research, vol. 41, pp. 2842–2848 (Jul. 1981).
Moses et al, Eur. J. Biochem., vol. 103, pp. 387–400 (1980).
Sporn et al, The New England Journal of Medicine, vol. 303, No. 15, pp. 878–880 (Oct. 9, 1980).
Niall et al, Journal of Surgical Research, vol. 33, pp. 164–169 (1982).
Stark et al, The Journal of Biological Chemistry, vol. 235, No. 11, pp. 3177–3181 (Nov. 1960).
Stromberg et al, Biochemical and Biophysical Research Communications, vol. 106, No. 2, pp. 354–361 (May 31, 1982).
Todaro et al, Proc. Natl. Acad. Sci. USA, vol. 77, No. 9, pp. 5258–5262 (Sep. 1980).
Twardzik et al, JNCI, vol. 69, No. 4, pp. 793–798 (Oct. 1982).
"Ion Exchange Chromatography", Pharmacia Fine Chemicals Brochure, pp. 43–47 and 61 (Mar. 1980).
"Gel Filtration Theory and Practice", Pharmacia Fine Chemicals Brochure, p. 44 (Mar. 1980).
Marshall et al, Practical Protein Chemistry A Handbook, Edited by Darbre, pp. 18–19 (1986).
Federation Proceedings, Abstracts, American Society of Biological Chemists, St. Louis, Missouri, May 31–Jun. 4, 1981, Peptides and Peptide Synthesis. p. 1643.
George J. Todaro, Journal of Supramolecular Structure and Cellular Biochemistry 15:287–301 (1981).
Anzano et al, Analytical Biochemistry, 125, pp. 217–224 (1982).
Brown et al, PNAS USA, 84, pp. 3743–3747 (1987).
DeLarco et al, PNAS USA, 75, No. 8, pp. 4001–4005 (1978).
DeLarco et al, Nature, vol. 272, pp. 356–358 (1978).
Holley et al, PNAS USA, vol. 77, No. 10, pp. 5989–5992 (1980).
Massaque et al, J. of Biol. Chem., vol. 260, pp. 4551–4554 (1985).
Marquardt et al, J. of Biol. Chem., vol. 255, No. 19, pp. 9177–9181 (1980).
Marquardt et al, J. of Biol. Chem., vol. 256, No. 13, pp. 6859–6862 (1981).
Moses et al, Oncogenes and Growth Control, Edited by P. Kahn and T. Graf, pp. 50–56 (1986).
Moses et al, Cancer Research, vol. 41, pp. 2842–2848 (1981).
Todaro et al, Cancer Research, vol. 38, pp. 4147–4154 (1978).
Tucker et al, Cancer Research, vol. 43, pp. 1581–1586 (1983).
Todaro et al, PNAS, vol. 77, pp. 5258–5262 (1980).
Roberts et al, PNAS, vol. 77, pp. 3494–3498 (1980).
Kovacina et al, Biochemical and Biophysical Research Communications, vol. 160, No. 1, pp. 393–403 (1989).
Variables in the High–Pressure Cation–Exchange Chromatography of Proteins, Charles A. Frolik, Analytical Biochemistry 125, 203–209 (1982).
High–Performance Liquid Chromatography of Proteins and Peptides, Proceedings of the First International Symposium, Milton T.W. Hearn, Academic Press.
Federation Proceedings, Abstracts 3478–6993, 66th Annual Meeting, Mar. 5, 1982, vol. 41, No. 4.
Anzano et al, Federation Proceedings, vol. 40, No. 6, p. 1643, Abstract No. 598 (May 1, 1981).
Sporn et al, Federation Proceedings, vol. 41, No. 5, Abstract No. 1288 (Mar. 5, 1982).
Roberts et al, PNAS USA, 78, No. 9, pp. 5339–5343 (Sep. 1981).
Frolik et al, Analytical Biochemistry, 125:203–209 (1982).
Todaro et al, Journal of Supramolecular Structure and Cellular Biochemistry, 15:287–301 (1981).
Anzano et al, Proc. of the First Intl. Symp. on HPLC of Proteins and Peptides, Washington, D.C., Nov. 16–17, 1981, Abstract No. 505.
Childs et al, PNAS usA, 79:5312–5316 (Sep. 1982).
Roberts et al, Nature, 295:417–419, Macmillan Journals Ltd., U.S. (1982).
Anzano et al, Cancer Research, 42(11), 4776–8 (1982).
Assoian et al, Federation Proceedings (USA), 42(7)1831 Abs. 428 (1983).
Frolik et al., PNAS, 80(12):3676–3680 (1983).
Assoian et al, J. Biol. Chem., 258(11):7155–7160 (1983).
Roberts et al, Federation Proceedings, 42(7):1832, Abs. 439 (1983).
Noe et al, Hormone Metab. Res., 7:314–22 (1975).
Permutt et al, J. Clin. Endocrin. Metab., 44:536–44 (1977).
Sporn et al, Science, 219:1329–31 (1983).
American Society of Biological Chemists, 74th Annual Meeting, Abstract Nos. 419, 420, 428, 439, 440 and 853, San Francisco, CA (Jun. 5–9, 1983).
Anzano et al, Proceedings of the First International Symposium, Hearn et al, ed., pp. 111–118 (Jan. 28, 1983).
Anzano et al, International Symposium HPLC Protein Peptide, #505, p. 25 (1981).
Brewer et al, Experimental Techniques in Biochemistry, P. 52 (1974).

Childs et al, Chemical Abstracts 97:142402j (1982).

De Larco et al, Journal of Cellular Physiology, 109:143–152 (1981).

Dicker et al, Chemical Abstracts, 95:201393r (1981).

Frolik et al, Biological Abstracts, 25:45382 (1983).

Massague, The Journal of Biological Chemistry, vol. 258, No. 22, pp. 13614–13620 (1983).

Moses et al, Cancer Research, vol. 41, pp. 2842–2848 (Jul. 1981).

Moses et al, Eur. J. Biochem., vol. 103, pp. 387–400 (1980).

Sporn et al, The New England Journal of Medicine, vol. 303, No. 15, pp. 878–880 (Oct. 9, 1980).

Niall et al, Journal of Surgical Research, vol. 33, pp. 164–169 (1982).

Stark et al, The Journal of Biological Chemistry, vol. 235, No. 11, pp. 3177–3181 (Nov. 1960).

Stromberg et al, Biochemical and Biophysical Research Communications, vol. 106, No. 2, pp. 354–361 (May 31, 1982).

Todaro et al, Proc. Natl. Acad. Sci. USA, vol. 77, No. 9, pp. 5258–5262 (Sep. 1980).

Twardzik et al, JNCI, vol. 69, No. 4, pp. 793–798 (Oct. 1982).

"Ion Exchange Chromatography", Pharmacia Fine Chemicals Brochure, pp. 43–47 and 61 (Mar. 1980).

"Gel Filtration Theory and Practice", Pharmacia Fine Chemicals Brochure, p. 44 (Mar. 1980).

Marshall et al, Practical Protein Chemistry A Handbook, Edited by Darbre, pp. 18–19 (1986).

PROMOTION OF CELL PROLIFERATION BY USE OF TRANSFORMING GROWTH FACTOR BETA (TGF-β)

CROSS-REFERENCE TO THE RELATED APPLICATIONS

This application is a continuation of Ser. No. 07/816,563 filed on Jan. 3, 1992, which is a divisional of Ser. No. 07/308,948 filed Feb. 8, 1989 (now U.S. Pat. No. 5,104,977, which issued on Apr. 14, 1992), which is a continuation of Ser. No. 06/581,021, filed Feb. 16, 1984 (now abandoned), which is a divisional of Ser. No. 06/500,833, filed Jun. 3, 1983 (now abandoned), which is a continuation-in-part of Ser. No. 06/468,590, filed Feb. 22, 1983 (now abandoned), which is a continuation-in-part of Ser. No. 06/423,203, filed Sep. 24, 1982 (now abandoned). This application is also related to application Ser. Nos. 06/500,832 and 06/500,927 which were filed on Jun. 3, 1983, The entire contents of all of the above applications are hereby incorporated by reference.

BACKGROUND OF THE INVENTION

1. Field of the Invention

This invention relates to compositions which promote repair of tissue, particularly fibroblast cells, in animals, particularly human beings. This invention further relates to a method of treating wounds by the topical or systemic administration of the compositions.

2. Description of the Prior Art

There is a continuing need for the promotion of rapid cell proliferation at the site of wounds, burns, diabetic and decubitus ulcers, and other traumata.

A number of "growth factors" are known, which promote the rapid growth of animal cells. These growth factors include epidermal growth factor (EGF), transforming growth factors (TGF's), and nerve growth factors (NGF). However, prior to this invention, none of these growth factors have been found to be pharmaceutically acceptable agents for the acceleration of wound healing.

It has been shown that the mitogenic activity of insulin (a hormone) can be increased many-fold by the presence of prostaglandin $F_{2\alpha}$ (not exactly a hormone, but having similar properties—it causes constriction of vascular smooth muscle), see L. Jimenez de Asua et al, *Cold Spring Harbor Conf. Cell Proliferation*, Vol. 6, Sato, ed., Cold Spring Harbor Labs., New York (1979) at pp. 403–424. Similar activation of insulin has been reported with fibroblast growth factor by P. S. Rudland et al, *Proc. Natl. Acad. Sci. USA*, 71, 2600–2604 (1974) and with EGF by R. W. Holley et al, *Proc. Natl. Acad. Sci. USA*, 71, 2908–2911 (1974). Furthermore, in the "competence-progression" scheme of C. D. Stiles et al, in *Proc. Natl. Acad. Sci. USA*, 76:1279–1283 (1979), positive effects on cell growth have been demonstrated for platelet-derived growth factor or fibroblast growth factor in combination with members of the insulin family such as somatomedins A and C, the insulin-like growth factors.

Many new peptide growth factors have been isolated and characterized recently, as indicated in *Tissue Growth Factors*, R. Baserga, ed., Springer-Verlag pub., New York (1981), however there have been few studies on the activity of these materials in vivo. In many cases, the relatively small amounts of peptides available have limited the ability to study their properties in vivo. An important area for potential application of peptide growth factors is the enhancement of wound healing. Despite the need for rapid wound healing in the treatment of severe burns, trauma, diabetic and decubitus ulcers, and many other conditions, at present there is no practical way to accelerate wound healing with pharmacological agents. Although it is suggested in *Tissue Growth Factors*, supra, at p. 123 that EGF might be of benefit in this area, it has yet to be extensively used in a practical way for wound healing.

SUMMARY OF THE INVENTION

This invention affords compositions for the promotion of cell proliferation in animals, especially fibroblast cells in human beings. The compositions have as their active ingredients, beta-type transforming growth factor (TGF-β) and an activating agent. The activating agents of this invention are selected from at least one of epidermal growth factor (EGF) and alpha-type transforming growth factor (TGF-α).

The TGF-β and the activating agent are preferably present in about equimolar amounts, and the active ingredients are present in an amount at least sufficient to stimulate cell proliferation (tissue repair).

As another embodiment, the activated TGF-β compositions of this invention may be admixed with other (secondary) growth factors to enhance their activity.

The compositions may be formulated in any suitable carrier for topical application, such as physiological saline solution or purified collagen suspension. The compositions also may be formulated in any suitable carrier for systemic administration.

The method of topical administration of the compositions of this invention is by direct application to a burn, wound, or other traumata situs. Periodic or continual further administration may be preferably indicated in most instances, since the active ingredients are physiologically utilized by the cells whose growth is being stimulated.

As a further embodiment, the compositions of this invention may be administered systemically by injection, enterally, transdermal patches, and the like, depending upon the nature and site of the traumata to be treated.

It has been discovered that platelets contain 40–100 fold more TGF-β than do the other non-neoplastic tissues examined to date. Complete purification of this platelet factor now shows that TGF-β is a polypeptide of about 25,000 daltons which is probably composed of two 12,500-dalton subunits held together by disulfide bonds. Its molecular weight, subunit structure, and amino acid composition differ from those of platelet-derived growth factor (PDGF). In contrast to most growth factors, platelet-derived TGF-β does not appear to exert its growth promoting property by directly stimulating total DNA synthesis.

Acidic ethanol extracts of human platelets induced non-neoplastic NRK-fibroblasts to undergo anchorage-independent growth. Less than 100 ng/ml of the crude extract elicits 50% of the maximal biological response when assayed in the presence of epidermal growth factor (2.5 ng/ml). In the absence of epidermal growth factor the potency of the extract decreased 1000-fold. These results show that platelets contain a type β transforming growth factor (TGF-β). The specific activity of the platelet extract is 100-fold greater than that of other non-neoplastic tissues. The growth factor was purified to homogeneity by sequential gel filtration, first in the absence and then in the presence of urea. These results, and its lack of strong mitogenic activity, show that this protein is distinct from platelet-derived growth factor. When completely purified, platelet derived TGF-β elicits 50% of its maximal biological response at concentrations less than $5\times10^{-12}$M.

A polypeptide transforming growth factor (TGF), which induces anchorage-dependent rat kidney fibroblasts to grow in soft agar,has been isolated from human placenta and purified to homogeneity. This polypeptide is classified as a type β TGF because it does not compete with epidermal growth factor (EGF) for membrane receptor sites but does require EGF for induction of anchorage-independent growth of indicator cells. Purification of this peptide was achieved by acid-ethanol extraction of the placenta, followed by gel filtration, cation-exchange and high-pressure liquid chromatography of the acid soluble proteins. Homogeneity of the TGF-β from the final column was shown by its constant specific activity and amino acid composition across the peak of soft agar colony forming activity and by its migration as a single band at 23,000 to 25,000 molecular weight after $NaDodSO_4$-polyacrylamide gel electrophoresis. Under reducing conditions, the protein migrated on a gel as a single band at 13,000 molecular weight. The purified placental TGF-β caused half maximal growth stimulation of indicator cells in soft agar at 64–72 pg/ml ($3\times10^{-12}$M) in the presence of 2 ng/ml ($3.4\times10^{-10}$M) of EGF.

DETAILED DESCRIPTION OF THE INVENTION

The term, "transforming growth factor" (TGF) has been defined to include the set of polypeptides which confer the transformed phenotype on untransformed indicator cells. The transformed phenotype is operationally defined by the loss of density-dependent inhibition of growth in monolayer, overgrowth in monolayer, characteristic change in cellular morphology, and acquisition of anchorage independence, with the resultant ability to grow in soft agar. Untransformed, non-neoplastic cells will not form progressively growing colonies in soft agar, while the property of anchorage-independent growth of cells in culture has a particularly high correlation with neoplastic growth in vivo.

Although TGFs were first discovered in the conditioned medium of virally-transformed neoplastic mouse cells, the application of the acid/ethanol method for extraction of peptides from tissues has now shown that TGFs can be found in almost all tissues, both neoplastic and non-neoplastic, from all species of animals that have been examined thus far. Although TGF activity is usually measured with an in vitro phenotypic transformation assay, this does not imply that TGF activity in vivo is necessarily related to the development of malignancy. Indeed, the transformed phenotype is a physiological state associated with normal embryological development, and transforming (onc) genes have been found in normal cells of essentially all vertebrates. The function of these onc genes from normal cells is not known at present. While there may be irreversible and excessive expression of TGF activity during malignant cell growth, the data at hand indicate that TGFs have a more benign and perhaps essential role in the function of normal cells. At present, it is not known what the intrinsic physiological roles of TGFs are. In this respect, TGFs are like many other peptide hormones or hormone-like agents which have recently been discovered and isolated; this is particularly true for many peptides of the nervous system, for which a defined chemical structure may be known, yet whose physiology is still a matter of uncertainty.

The initial description of sarcoma growth factor (SGF), the first of the TGFs to be isolated, was an important finding in tumor cell biology since it provided a direct mechanism for the expression of the neoplastic phenotype in a vitally-transformed cell. Two important properties of SGF were described in these earliest studies, namely (1) that the effects of SGF in causing phenotypic transformation were dependent on its continued presence, and that these effects were reversible when SGF was removed, and (2) that the effects of SGF could be expressed in the very same cells that synthesized this peptide, a property that has been termed autocrine secretion. Although these two properties have not been definitively shown for all of the other more newly discovered TGFs, the functions of the entire set of TGFs can most reasonably be assumed to be that of local, hormone-like agents that reversibly control cell function by paracrine or autocrine mechanisms.

Since the discovery of SGF in 1978, many TGFs have been described from diverse sources. These TGFs can be categorized into two groups: extracellular TGFs isolated from conditioned media of cultured cells, and intracellular (cell-associated) TGFs isolated by direct extraction of cells or tissues. Although extracellular TGFs have recently been isolated from non-neoplastic murine cells, use of conditioned medium has, in general, been restricted to neoplastic cell lines that could be grown in long-term, large-scale culture, including certain vitally and chemically-transformed rodent cells and human tumor cell lines. The adaptation of an acid/ethanol extraction procedure to TGF isolation removed all limitations on cell types and quantities of tissues that could be examined. Using this procedure, extracts of all tissues or cells, whether of neoplastic or non-neoplastic origin, whether from adult or embryonic tissue, whether from human, bovine, or murine genomes, have been shown to promote colony formation in a soft agar assay; hence, by definition, these extracts contain TGF activity.

A variety of both epithelial and fibroblastic cell lines form colonies in soft agar in the presence of TGFs. However, the most commonly used indicator cell line is the rat kidney fibroblast cell clone, NRK 49F, which has been selected for its strong colony-forming response to the TGFs. Rat-1 cells and mouse AKR-2B cells have also been used successfully as indicator cells.

All of the TGFs referred to above are low molecular weight polypeptides which share with SGF the physical properties of acid and heat stability and sensitivity to treatment with both trypsin and dithiothreitol. However, there are marked differences in the biological properties of these TGFs, particularly with respect to their relationship to EGF. Certain TGFs, though antigenically distinct from EGF, have some structural homology to EGF, since they compete with EGF for receptor binding. Other TGFs do not compete with EGF for receptor binding, but instead are dependent on EGF for activity in the soft agar assay for colony formation. To remove the ambiguities implicit in the assignment of the general term "TGF" to these different factors, an operational classification of the members of the TGF family based on their interactions with EGF is suggested, both with respect to competition for binding to the EGF receptor and to the requirement for EGF for induction of colonies in soft agar.

As defined for purposes of this invention, TGF-α are those TGFs which compete with EGF for receptor binding and which do not require EGF for the induction of colony formation in soft agar. TGFs with these properties include SGF and other TGFs derived from neoplastic cells, as well as some TGFs from mouse embryos.

As defined for purposes of this invention, TGF-β are those TGFs which do not compete with EGF for receptor binding and which require EGF for the induction of colony growth in soft agar. When assayed in the presence of EGF, TGF-β represents the major colony-forming activity of the intracellular TGFs of both neoplastic and non-neoplastic cell lines and tissues. It can be assumed that TGF-β will be found in conditioned media as well, once the proper assays are used.

Those TGFs which do not compete with EGF for receptor binding and which do not require EGF for colony formation are designated TGF-γ (gamma-type TGF). Such TGFs have been described in conditioned media of certain virally or chemically transformed cells. Finally, TGF-δ (delta-type TGF) is used to specify those TGFs which would both compete for EGF receptors and require EGF for colony formation in soft agar. EGF itself could be classified as a weak TGF-δ.

Example of Purification and Properties

Research in our laboratory has been directed toward the isolation of TGFs directly from cells and tissues. An acid/ethanol extraction procedure was modified for this purpose, as disclosed in A. B. Roberts et al, *Proc. Natl. Acad. Sci. USA*, 77:3494–3498 (1980), and chromatography and high pressure liquid chromatography (HPLC) have been employed for further purification. TGF activity, measured by the ability to induce non-neoplastic indicator cells (NRK) to form colonies in soft agar, has been quantitated on an image analysis system with respect to both the number and size of the colonies formed. By use of HPLC, we have shown that two distinctly different TGFs, here classified as TGF-α and TGF-β, can be isolated from the same pool of acid/ethanol extracts of MSV-transformed 3T3 cells; for this purpose, columns using a linear gradient of acetonitrile in 0.1% trifluoroacetic acid have been used. TGF-α, which elutes from the column earlier than marker EGF, is characterized by its ability to induce the formation of small colonies (850-3,100 μm$^2$) in soft agar in the absence of added EGF and its ability to compete with EGF in a radio-receptor assay. TGF-β, which elutes later than TGF-α or marker EGF, does not compete with EGF for receptor binding and requires EGF to induce the formation of large colonies (>3,100 μm$^2$) in the soft agar assay.

TGF-α from MSV-transformed 3T3 cells resembles SGF isolated from the conditioned medium of the same cells and other TGFs isolated from rat and human tumor cell lines. Recently, SGF and the TGF-α's from the conditioned media of a human melanoma cell line and virally-transformed rat embryo fibroblasts have been purified to homogeneity. The human melanoma TGF-α is a single chain polypeptide of molecular weight 7,400. Its amino acid composition and chromatographic behavior are markedly different from that of human EGF, but similar to that of murine SGF and rat TGF-α, suggesting that TGF-α's from human, rat and mouse genomes are more closely related to each other than to EGF. There is therefore a reasonable possibility that TGF-α's may have cross-species utility.

In sarcoma virus-transformed rodent cell lines, the release of TGF-α into the medium has been correlated with the expression of the transformed phenotype, and within a selected set of human tumor cell lines that release TGF-α, the ability of the tumor cells to grow in soft agar has been correlated with the quantity of TGF-α they secrete. However, secretion of TGF-α is not an absolute requirement for neoplastic behavior; certain chemically transformed murine cell lines and human lung carcinoma cell lines that do not secrete TGF-α release strong TGF activity that does not compete with EGF for receptor binding.

TGF-β of the acid/ethanol extract of the MSV-transformed 3T3 cells resembles other TGFs isolated from many neoplastic and non-neoplastic tissues. After further purification on a second HPLC column, TGF-β of the MSV-transformed cells eluted at the same position in the n-propanol gradient (48%) as one peak of TGF-β activity of the bovine salivary gland, and each was associated with a small peak of absorbance at 280 nm. These two TGF-β's, one from a neoplastic mouse cell line and the other from a non-neoplastic bovine tissue, each migrated as a 12,500–13,000 daltons MW protein on SDS-PAGE in the presence of mercaptoethanol and as an apparent 25,000–26,000 daltons protein in the absence of mercaptoethanol; they therefore appear to be closely related to each other and different from both TGF-α and EGF. The finding of TGF-β in all non-neoplastic tissues examined thus far suggests a normal physiological function for these TGFs. There is therefore a reasonable possibility that TGF-β's may have cross-species utility.

Amino Acid Composition and Sequencing of TGF-β

Through a combination of techniques, TGF-β from bovine kidneys was purified 200,000-fold to the point of homogeneity.

For amino-terminal sequence analysis, approximately 500 picomoles ($M_r$ 25,000) of TGF-β were reduced and S-carboxymethylated with dithiothreitol and iodo-[$^{14}$C] acetic acid in the presence of 6M guanidine-HCl in 1M Tris-HCl buffer, pH 8.4. Excess reagents were separated from carboxymethylated protein by HPLC on a 5 micron 50×4.6 mm column eluted with a gradient of 0–90% acetonitrile (1% per min) in 0.1% TFA. Overall recovery of the procedure was 96%, based on estimating the amount of protein by amino acid analysis using fluorescamine detection.

Automated Edman degradation was performed on about 500 pmoles ($M_r$ 12,500) of the S-carboxymethylated protein with a gas-phase sequencer. PTH-amino acids were identified using an HPLC system. Initial yield was about 30% and repetitive yield about 90%.

Analysis of the bovine kidney TGF-β by electrophoresis on NaDodSO$_4$-polyacrylamide gels suggests that some of the disulfide bonds are interchain.

Amino acid sequence analysis of the reduced and S-carboxymethylated bovine kidney TGF-β by automated Edman degradation using a gas-phase sequencer revealed a single N-terminal amino acid sequence as follows, (CMC is S-carboxymethylcysteine):

$$\underset{}{\text{Ala}}-\text{Leu}-\text{Asp}-\text{Thr}-\overset{5}{\text{Asn}}-\text{Tyr}-\text{CMC}-\text{Phe}-\text{Ser}-\overset{10}{\text{Ser}}-\text{Thr}-\text{Glu}-$$

$$\overset{15}{\text{Lys}}-\text{Asn}-\text{CMC}-.$$

Initial and repetitive yields were found to be equal to the yields calculated for myoglobin used as standard protein. At the minimum, the results indicate that the sequence of at least the first fifteen N-terminal amino acids of each of the two subunits of TGF-β is identical and confirm the observations of a single protein band of the reduced TGF-β on NaDodSO$_4$-polyacrylamide gels. In addition, the N-terminal sequence of the bovine kidney TGF-β is identical to the partial sequence of TGF-β from human placenta, suggesting a high degree of relatedness of type β TGFs from different species and different tissue sources.

Activation of TGF-β

Recent experiments in our laboratory have shown that either TGF-α or EGF will activate TGF-β to induce the formation of large colonies in soft agar. Purified TGF-β from the MSV-transformed 3T3 cells, assayed by itself, had no colony-forming activity at concentrations as high as 2 µg/ml. However, assayed after activation by the presence of either EGF, or TGF-α derived from the same cells, TGF-β induced a dose-dependent formation of large colonies (>3,100 µm$^2$) at concentrations of 10–200 ng/ml. By contrast, EGF or TGF-α, assayed by themselves, induced a maximal response of only a small number of colonies; this response was increased 10-fold by the addition of TGF-β. The relative abilities of EGF and TGF-α to promote TGF-β-dependant formation of large colonies in soft agar correlated with their relative abilities to compete for binding to the EGF receptor; other experiments using chemically-modified EGF analogues have substantiated this correlation. These data, demonstrating that the induction of a strong colony-forming response requires both TGF-α and TGF-β or EGF, suggest that TGF-β, which is found in all tissues, may be an essential mediator of the effects of TGF-α and of EGF on neoplastic transformation.

Little is known about the mechanisms by which exogenous TGFs induce non-neoplastic cells to express the transformed phenotype. Furthermore, the synergistic interactions of TGF-α and TGF-β suggest that these two TGFs may act through different pathways. Experiments using TGFs of conditioned media of sarcoma virus-transformed rodent cells have shown that the synthesis of new RNA and protein is required before transformation occurs. Other experiments have been directed at a possible role of TGFs in phosphorylation reactions. Certain viral transforming gene products and their normal cellular homologues have tyrosine-specific protein kinase activity, and it has been proposed that phosphorylation at tyrosine of specific substrates may be important in the transformation process. Treatment of human carcinoma A431 cells with various TGFs derived from conditioned media of virally-transformed cells or human tumor cell lines (TGF-α) resulted in phosphorylation of tyrosine residues in the 160K EGF receptor. The pattern of phosphorylation, however, was indistinguishable from that induced by EGF itself, and thus would not appear to be transformation-specific. Likewise, dissolution of actin fibers of Rat-1 cells occurs when they are treated with either TGF or EGF. It is clear that further research is needed to establish the relationships of the TGFs to the retrovirus transforming gene products and the mode of action of the TGFs in neoplastic transformation.

The following are summaries of examples which illustrate various aspects of this invention:

EXAMPLE 1

HPLC separation of TGF-α and TGF-β of MSV-transformed 3T3 cells.

The acid/ethanol extract of MSV-transformed cells was chromatographed on Bio-Gel P-30 in 1M acetic acid. The 7–10,000 MW TGF fraction was further purified on a µBondapak C18 column using a gradient of acetonitrile in 0.1% trifluoroacetic acid. Aliquots were assayed for colony-forming activity in the soft agar assay; in the presence of 2 ng/ml EGF; and in competition with $^{125}$I-EGF in a radio-receptor assay.

EXAMPLE 2

HPLC purification on µBondapak CN columns of TGF-β from MSV-transformed mouse 3T3 cells and bovine salivary gland using a gradient of n-propanol in 0.1% trifluoroacetic acid.

TGF-β of acid/ethanol extracts was purified on Bio-Gel P-30 and µBondapak C18 columns and then applied to CN columns. Aliquots were assayed for induction of colony growth of NRK cells in soft agar in the presence of 2 ng/ml EGF.

EXAMPLE 3

Synergistic interaction (activation) of TGF-β with TGF-α to induce the formation of large colonies of NRK cells in soft agar.

Soft agar colony-forming activity of varying concentrations of µBondapak CN-purified TGF-β derived from MSV-transformed 3T3 cells was assayed either alone or in the presence of either CN-purified TGF-α derived from the same cells or murine EGF. Soft agar colony-forming activity of varying concentrations of EGF or TGF-α was assayed either alone or in the presence of TGF-β.

In Vivo Demonstration of Wound Healing

After the above in vitro demonstrations of the operability of the compositions of this invention, it was considered critical to confirm that the compositions could work in clinical applications. For this purpose, TGFs were isolated on a relatively large scale from bovine sources and the wound healing activity of the compositions according to this invention was satisfactorily demonstrated using an experimental rodent wound healing protocol.

The examples which follow demonstrate not only that the compositions according to this invention are effective in vivo, but also that TGFs may be employed cross-species.

EXAMPLE 4

Purification and separation of TGF-α and TGF-β.

Bovine tissues, obtained fresh from the slaughterhouse and frozen immediately on dry ice, were extracted in 2 kg batches with acid/ethanol in accordance with A. B. Roberts et al, *Proc. Natl. Acad. Sci. USA*, 77:3494 (1980). Extracts from 6–8 kg tissue were combined and chromatographed on Bio-Gel P-30 with 1M acetic acid, using an 80 liter bed volume column. The TGFs of extracts of bovine kidney or bovine salivary gland eluted in a broad peak between the RNase (13,700) and insulin (5,700) markers, as had been observed for the TGFs of mouse kidney and mouse salivary gland. TGFs at this stage of purification had a specific activity approximately 10 to 25-fold higher than the acid/ethanol extracts, with a range of recovery of 150,000–200,000 colony-forming units per kg tissue. Most of the in vivo studies reported below were done with salivary gland or kidney TGFs purified to this stage. The TGF's activity in vitro was enhanced approximately 20-fold by the presence of 2–5 ng EGF per ml in the assay, in accordance with this invention.

Following chromatography on Bio-Gel P-30, the bovine TGF-β were purified further by High Pressure Liquid Chromatography (HPLC) on μBondapak C18 columns using an acetonitrile gradient in 0.1 percent trifluoroacetic acid, followed by a second HPLC step on μBondapak CN columns using a gradient of n-propanol in 0.1 percent trifluoroacetic acid. After the two HPLC steps, analysis of the bovine TGF-β's from both salivary gland and kidney by sodium dodecyl sulfate polyacrylamide gel electrophoresis under reducing conditions showed a single band with an apparent molecular weight of 13,000 daltons. At this stage of purification, each of the bovine TGF-β's had an absolute requirement for EGF for colony-forming activity. The yield of HPLC-purified TGF-β was approximately 20–100 μg per kg tissue, with a total activity of 7,000–18,000 colony-forming units.

EXAMPLE 5

Wound Healing Protocol.

In vivo activity of isolated salivary gland TGF-β and kidney TGF-β was measured in accordance with the protocol described by T. K. Hunt et al, *Amer. J. Surgery*, 114:302 (1967). Six empty Schilling-Hung wire mesh wound chambers were surgically inserted subcutaneously in the backs of rats, in paired symmetrical fashion (A-D, B-E, C-F) as shown below:

TABLE 1

| head | |
|---|---|
| A | D |
| B | E |
| C | F |
| tail | |

The rats respond to these chambers as if they were wounds, and eventually the chambers become filled with fibroblasts and collagen. By the fourth day after insertion, the chambers become encapsulated with connective tissue, but there are few cells within the chambers themselves. There is thus a defined, enclosed space within the chambers, where a wound healing response can be quantitatively measured. At this time, daily injections of TGF-β (0.1 ml, in sterile phosphate-buffered saline) into chambers A, B, and C were begun. To activate TGF-β activity, a low level of murine EGF was included in all TGF-β injections, unless noted otherwise. Chambers D, E, and F were used as controls, and were injected with either an amount of bovine serum albumin (BSA) alone or in combination with either TGF-β or EGF, such that the total protein was equivalent to the amount of TGF-β injected into chambers A, B, and C. Injections were made once daily for either 5 days (Table 1) or 9 days (Table 3). All injected materials were sterile. The rats were sacrificed 6 hours after the last TGF-β injection; in Table 2 they were injected with 0.5 mCi of thymidine-$^3$H, specific activity 6.7 Ci/millimole (i.p.) together with the last TGF-β injection. The chambers were removed from the rats, all connective tissues on the outside of the wire mesh was peeled away, and then the contents of each chamber were determined.

TABLE 2

Wound healing response to bovine salivary gland or kidney TGF after 5 days of treatment. TGF-βs were prepared and injected as described. Each dose contained 25 times the amount of TGF-β found optimal for colony formation by NRK cells in a standard soft agar assay, and ranged from 18–42 colony forming units per dose. The amounts of protein injected per dose were: 7 μg in Expts. 1, 4 and 5; 25 μg in Expt. 3, and 0.7 μg in Expt. 2. All doses of EGF were 20 ng. Total protein in wound chambers was measured by the method of Lowry et al.** Statistical analysis of the data was made by comparison of matched pairs of the chambers (A vs. D, B vs. E, C vs. F) shown in Table 2.

| Expt. | Chamber A, B, C treatment | Chamber D, E, F treatment | Number of matched pairs of chambers | Milligrams of protein per chamber, average (15) A, B, C | Milligrams of protein per chamber, average (15) D, E, F | Average ratio ± standard error of mean* | P |
|---|---|---|---|---|---|---|---|
| 1 | TGF-β (Salivary P-30) + EGF | BSA | 36 | 10 | 3.9 | 3.8 ± 0.6 | <0.001 |
| 2 | TGF-β (Salivary HPLC) + EGF | BSA | 9 | 8.4 | 2.9 | 4.6 ± 1.0 | <0.02 |
| 3 | TGF-β (Kidney P-30) + EGF | BSA | 9 | 8.1 | 3.5 | 5.2 ± 1.5 | <0.005 |
| 4 | TGF-β (Salivary P-30) + EGF | EGF | 9 | 9.6 | 5.3 | 2.1 ± 0.3 | <0.02 |
| 5 | TGF-β (Salivary P-30) + EGF | TGF-β | 9 | 11.2 | 9.6 | 1.4 ± 0.3 | 0.5 |

*Average of each matched pair ratio, A/D, B/E, C/F
One sided P values based on the sign test
**J. Biol. Chem., 193:265 (1951)

TABLE 3

Wound healing response to bovine salivary gland TGF-β after 9 days of treatment.
Chambers A, B, and C were dosed once daily with 7 μg of TGF-β (P-30) plus 20 ng of EGF.
Chambers D, E and F were dosed with an equal amount of BSA.

| Measurement | Number of matched pairs of chambers | Average content per chamber A, B, C, | Average content per chamber D, E, F | Average ratio ± standard error of mean* | P |
|---|---|---|---|---|---|
| Protein, milligrams | 30 | 24 | 15 | 1.6 ± 0.05 | <0.001 |
| DNA, micrograms | 30 | 21 | 8.6 | 2.6 ± 0.16 | <0.001 |
| Thymidine-$^3$H, cpm per microgram of DNA | 30 | 45 | 30 | 1.7 ± 0.09 | <0.001 |
| Collagen, milligrams | 9 | 5.2 | 3.2 | 1.8 ± 0.2 | <0.005 |

*Average of each matched ratio pair, A/D, B/E, C/F
One sided P values based on the sign test Table 1 shows that 5 days of treatment of rats with TGF-β from either bovine salivary gland or bovine kidney caused a significant increase in total protein in the treated chambers, as compared to control chambers treated with an equivalent amount of bovine serum albumin (Experiments 1, 3). The salivary gland TGF-β was still highly active after two steps of purification by the high pressure liquid chromatography (Experiment 2). The effects observed are not the sole result of the minute amounts of EGF which had been used to potentiate the activity of TGF-β, since a highly significant difference between treated chambers A, B and C, compared to control chambers D, E and F was still observed when EGF was used at the control substance (Experiment 4). Furthermore, when all chambers were treated with TGF-β, and only A, B and C were treated with EGF, no significant difference was observed (Experiment 5). At the end of Experiments 1–4, it was consistently observed that chambers A, B and C were more firmly fixed in the surrounding connective tissue than the respective matched control chambers, suggesting that effects of the TGF-β also were manifested in the area immediately surrounding the chambers.

In order to measure the effects of bovine salivary TGF-β on DNA and collagen content of the chambers, it was necessary to treat the animals for longer than 5 days. Table 2 shows the results of a larger experiment in which 13 rats were treated for 9 days. The increases in total protein, total DNA, thymidine incorporation into DNA, and total collagen were all highly sufficient. Histological examination of the contents of the chambers treated with TGF-β confirmed the occurrence of fibroblastic proliferation and formation of collagen. A sterile infiltrate of inflammatory cells was also found within both treated and control chambers.

The results obtained in both experiments indicate that TGF-βs when activated in accordance with this invention, can significantly accelerate a wound healing response.

Clinical Use of the Compositions of This Invention

The compositions of this invention, whose active ingredients are TGF-β activated by at least one of a TGF-α and an EGF, can reasonably be expected to have clinical use in the treatment of animals, particularly mammals, most particularly human beings. There are several sound bases for this conclusion.

It has been shown above, that in in vitro tests, the compositions can markedly increase the growth of cells without changing their genotype. An important characteristic of the components of the compositions of this invention, is that they do not appear to be species specific. That is, TGF-β from one species can be activated by TGF-α and/or EGF from other species. The cells whose growth is promoted can be of any type such as fibroblast or epithelial, although it is considered that the growth promotion of fibroblast cells will have the greatest medical utility.

The in vivo experimental protocol disclosed above, with its very favorable results, clearly indicates that the compositions of this invention have utility in the treatment of traumata by the rapid promotion of the proliferation of the cells surrounding the traumata.

Two types of application of the compositions of this invention are contemplated.

The first, and preferred, application is topically for the promotion of surface wound healing. There are no limitations as to the type of wound or other traumata that can be treated, and these include (but are not limited to): first, second and third degree burns (especially second and third degree); surgical incisions, including those of cosmetic surgery; wounds, including lacerations, incisions, and penetrations; and surface ulcers including decubital (bed-sores), diabetic, dental, haemophiliac, and varicose. Although the primary concern is the healing of major wounds by fibroblast cell regeneration, it is contemplated that the compositions may also be useful for minor wounds, and for cosmetic regeneration of cells such as epithelial. It is also contemplated that the compositions may be utilized by the topical application to internal surgical incisions.

When applied topically, the compositions may be combined with other ingredients, such as carriers and/or adjuvants. There are no limitations on the nature of such other ingredients, except that they must be pharmaceutically acceptable, efficacious for their intended administration, and cannot degrade the activity of the active ingredients of the compositions. When the compositions of this invention are applied to burns, they may be in the form of an irrigant, preferably in combination with physiological saline solution. The compositions can also be in the form of ointments or suspensions, preferably in combination with purified collagen. The compositions also may be impregnated into transdermal patches, plasters, and bandages, preferably in a liquid or semi-liquid form.

The second application is systemically for the healing of internal wounds and similar traumata. Such an application is useful provided that there are no, or limited, undesirable side-effects, such as the stimulation of neoplastic cellular growth.

When applied systemically, the compositions may be formulated as liquids, pills, tablets, lozenges, or the like, for enteral administration, or in liquid form for parenteral injection. The active ingredients may be combined with other ingredients such as carriers and/or adjuvants. There are no limitations on the nature of such other ingredients, except that they must be pharmaceutically acceptable, efficacious for their intended administration, and cannot degrade the activity of the active ingredients of the compositions.

The amount of activating agent (TGF-αs or EGFs) present depends directly upon the amount of TGF-αs present in the activated compositions of this invention. There are indications that the activation is not catalytic in nature, and that therefore approximately stoichiometric (equimolar) quantities are preferred.

The amount of activated composition to be used in the methods of this invention cannot be stated because of the nature of the activity of TGFs and the nature of healing wounds and/or other traumata. As indicated above, the TGFs activate cells by binding to receptor sites on the cells, after which the TGFs are absorbed and utilized by the cells for the synthesis of new protein, resulting in cell multiplication. Thus, the TGFs are consumed by the cell regenerating process itself, rather than acting in an enzymatic or other catalytic manner. Receptors for EGFs have been found on a wide variety of fibroblastic, epithelial, and parietal cells, as disclosed in Gonzalez et al, *J. Cell. Biol.*, 88:108–144 (1981). Further, it has been calculated that there are 3,000 EGF binding (receptor) sites for each rat intestinal epithelial cell, as disclosed in M. E. Lafitte et al, *FEBS Lett.*, 114(2):243–246 (1980). It must also be obvious that the amount of a cell growth promoting substance (such as the compositions of this invention) that must be utilized will vary with the size of the wound or other traumata to be treated.

Since the compositions of this invention both provoke and sustain cellular regeneration, a continual application or periodic reapplication or the compositions is indicated.

The amount of active ingredient per unit volume of combined medication for administration is also very difficult to specify, because it depends upon the amount of active ingredients that are afforded directly to the regenerating cells of the wound or other traumata situs. However, it can generally be stated that the TGF-βs should preferably be present in an amount of at least about 1.0 nanogram per milliliter of combined composition, more preferably in an amount up to about 1.0 milligram per milliliter.

Additional Embodiments Utilizing the Compositions of this Invention

In addition to utilizing the activated TGF-β compositions of this invention by themselves, it is possible to use them in combination with secondary growth factors.

The activated transforming growth factors of this invention may be physically admixed with one or more of many other (secondary) peptide and non-peptide growth factors. Such admixtures may be administered in the same manner and for the same purposes as the activated transforming growth factors of this invention utilized alone to enhance their activity in promoting cell proliferation and repair.

The useful proportions of activated transforming growth factor to secondary growth factors are 1:0.1–10 mols, with about equimolar amounts being preferred.

The secondary growth factors may be used alone or in any physiologically and pharmaceutically compatible combination.

The known secondary growth factors, in approximately descending order of usefulness in this invention (by group), include:

1. platelet-derived growth factors.
2. fibroblast growth factors angiogenesis factors
3. insulin-like growth factors including somatomedins
4. insulin nerve growth factors
5. anabolic steroids.

In addition to the above known secondary growth factors, it is reasonable to expect that as yet undiscovered secondary growth factors will be useful in admixture.

This invention also incorporates the inactive intermediate substance TGF-β per se. Prior to this invention, this substance had not been isolated or identified. TGF-β is believed to be substantially the same or very similar for each animal species, regardless of the individual of that species or the particular body cells from which it is derived. Since TGF-β has been shown to be non-species-specific between rodents, cattle, and human beings, it is also reasonable to believe that the substance is substantially the same or very similar when derived from any mammal, and possibly from any animal source. It should be noted, moreover, that this invention includes TGF-β regardless of the source from which it is isolated or derived, including genetically engineered cells. It is well within the capabilities of biochemical technology to genetically engineer a cell to produce TGF-β at the present time.

Administration of Unactivated TGF-β

It is believed that TGF-β has no wound-healing or other tissue-repair activity unless it has been activated by an agent as described above.

However, it is noted that Table 2 Experiment 5, supra, appears to indicate statistically similar results for TGF-β activated with EGF (chambers A, B, C) and TGF-β per se (chambers D, E, F). The most logical explanation for this, is that the TGF-β per se was activated by a TGF already present in the test animal. Various TGFs, such as EGF, are known to be present in blood plasma.

Thus, the results of Experiment 5 are not inconsistent with this invention, but instead constitute a variant embodiment thereof. Specifically, TGF-β per se may be administered, in accordance with this invention, instead of activated TGF-β, when there are sufficient endogenous activating agents present in an animal, to activate an amount of TGF-β sufficient to promote cell proliferation and tissue repair. It is anticipated that in an animal suffering from the traumata contemplated herein, there usually will not be sufficient endogenous activating agents present.

The disclosures of the following applications, which were filed on the same date as the present continuation-in-part application, i.e., Jun. 3, 1983, are entirely incorporated herein by reference:

1. "Transforming Growth Factor-beta From Human Platelets", by Richard K. Assoian, Charles A. Frolik, Michael B. Sporn and Anita B. Roberts, U.S. Ser. No. 500,832 (now abandoned).
2. "Transforming Growth Factor-beta From Human Placentas", by Charles A. Frolik, Richard K. Assoian, Michael B. Sporn, and Anita B. Roberts, U.S. Ser. No. 500,927 (now abandoned).

EXAMPLE 6

TGF-β From Human Platelets Ser. No. 06/500,832)

Transforming growth factors have been detected in a variety of non-neoplastic tissues, but major sites of storage have not been identified. However, a comparison of both specific activities in initial extracts and yields of purified TGF-β, shows that platelets are a major storage site for the growth factor; they contain 40–100 fold more TGF-β than do the other non-neoplastic tissues which have been examined. This finding, in conjunction with the known role of platelets in wound healing, supports the hypothesis that at least one physiological role of TGF-β is to facilitate tissue repair and regeneration.

The total purification of platelet-derived TGF-β was facilitated by both the high specific activity of the platelet extract and the aberrant elution of the polypeptide during gel filtration. Contaminants with molecular weights similar to a column of the TGF (25,000 daltons) were removed on acrylamide gel in 1M acetic acid. In this system TGF-β elutes with proteins of half its mass. (An apparent discrepancy in one fraction—high biological activity and no detectable protein at 25,000 daltons—was due to the fact that detection of TGF-β by bioassay is at least 100-fold more sensitive than chemical detection of the protein by electrophoresis and silver staining). Addition of urea to the eluant prevented this retardation and resulted in the complete separation of TGF-β from the lower molecular weight peptides. The overall recovery of biological activity from the purification procedure is somewhat low (about 5%), but control studies showed that other platelet factors modulate TGF-β action. (The specific activity of TGF-β decreased at least 10-fold when it was assayed in medium containing 10% plasma-derived rather than whole-blood derived serum; data not shown). Removal of these factors during the purification procedure may well explain the observed decreases in total TGF-β biological activity. The maximal biological activity of PDGF also requires the presence of other bio-active peptides.

Purified, platelet-derived TGF-β was characterized chemically and biologically (Tables 4 and 5). Its molecular weight (25,000 daltons), subunit structure (two 12,500-dalton polypeptides indistinguishable by SDS-polyacrylamide gel electrophoresis), and amino acid composition differ from that of PDGF. Moreover, PDGF is a potent mitogen whereas platelet-derived TGF-β is, at best, weakly mitogenic. Using similar biochemical criteria platelet-derived TGF-β is also distinct from the platelet protein family comprised of CTAP-III, β-thromboglobulin, and platelet factor 4.

The role of platelets as a source of growth factors has received widespread attention since the identification of PDGF. A platelet-derived peptide (C-TAP III; 9300 daltons) has been purified to homogeneity and shown to be mitogenic for connective tissue cells. Two platelet growth factors distinct from PDGF have been identified on the basis of their isoelectric points. Recently, it has been shown that TGF activity is present in platelets and that the activity is enhanced by EGF. These studies with partially purified preparations yielded two active components during gel filtration ($M_r$=12–16,000 and 6,000). The larger protein is likely the 25,000 dalton TGF-β described herein eluting with an aberrantly low molecular weight during gel filtration in the absence of denaturant. The smaller TGF was not detected but attention has been focused only on the most active TGF species in platelets. Transforming growth factors having specific activities less than 10% of that of the 25,000-dalton TGF-β would not be detected with the activity limits imposed herein.

Studies implicating PDGF in atherosclerosis and control of cell division have emphasized its physiological release from platelets during their aggregation at a site of injury. However, the characterization of PDGF as a competence factor suggests that platelet-mediated control of cell growth likely involves a complex synergism between several bioactive peptides. Platelet-derived TGF-β has strong growth promoting ability, but it is not a strong mitogen. This unusual combination of biological properties suggests that this protein may play a unique role in those physiological and pathological processes where platelet-derived factors modulate cell proliferation.

Examples of Platelet Derived TGF-β Purification and Analysis

Platelet Extraction:

Platelet concentrates (20–30 units, 2–5 days old) were obtained through the courtesy of the National Institutes of Health Blood Bank (Bethesda, Md., U.S.A.) and centrifuged (3200×g, 30 min.) to remove remaining plasma proteins. The platelets were washed twice by suspension in 500-ml portions of Tris-HCl/citrate buffer, pH 7.5, and centrifugation as described above. Washed platelets (20–30 g wet weights) were added to a solution of acidic ethanol prepared as described elsewhere and immediately extracted in a homogenizer (4 ml acidic ethanol per g platelets). After incubation overnight at 4° C., precipitated proteins were removed by centrifugation, and the resulting supernatant was adjusted to pH 3 by addition of $NH_4OH$. Proteins and TGF activity were precipitated from the solution (overnight at 4° C.) by addition of ethanol (2 vol, 0° C.) and ethyl ether (4 vol, 0° C.). The precipitate was collected by centrifugation and suspended in 1M acetic acid (10 ml). TGF activity was solubilized during an overnight extraction at 4° C. Centrifugation clarified the solution; the supernatant was freeze-dried or subjected directly to gel filtration. The amount of protein in the extract was determined by weight or by reaction with Coomassie Blue using bovine plasma albumin as reference.

Purification of Platelet-Derived TGF-β:

The solubilized platelet extract (10 ml in 1M acetic acid) was gel-filtered at a flow rate of 20 ml/h on a column (4.4×115 cm) of acrylamide gel equilibrated in 1M acetic acid. Fractions containing 5 ml were collected. The elution position of TGF-β was determined by bioassay as described below, and the fractions containing the peak of activity were pooled and freeze-dried. The amount of protein in the pool was determined as described above. The residue was dissolved in 0.5 ml of 1M acetic acid containing 8M ultra-pure urea and gel-filtered at a flow rate of 3 ml/h on a column (1.6×85 cm) of acrylamide gel which had been equilibrated in the sample solvent. Fractions containing 0.5 ml were collected. (To preclude the formation of cyanate in the solvent, the ultra-pure urea was dissolved at pH 2 in 1M acetic acid. The resulting solution was adjusted to final conditions by addition of glacial acetic acid and water). Aliquots of selected column fractions were tested for TGF-β activity. Fractions containing the peak of TGF-β activity were pooled, dialyzed against 1M acetic acid to remove urea, and quick-frozen for storage at −20° C. The amount of TGF-β in the final solution was determined by amino acid analysis (see below).

Bio-assay of TGF-β:

The bioassay of TGF-β determines the ability of the polypeptide to induce anchorage-independent growth in non-neoplastic NRK-fibroblasts by measuring the formation of colonies of cells in soft agar. The assay was performed as described in Roberts et al, Proc. Nat. Acad. Sci. U.S.A., 77:3494–3498 (1980) except that 1) 3500 cells were used per dish, 2) incubation proceeded for 7 days at 37° C. in a humidified atmosphere of 10% $CO_2$ in air, and 3) TGF-β activity was determined in the presence of EGF (2.5 ng/ml). Samples were sterilized in 1M acetic acid and freeze-dried in the presence of bovine serum albumin (100 µg) as carrier prior to analysis. Stained colonies were quantitated by number and size. One unit of TGF-β activity is defined as that biological response resulting in 50% of maximal colony formation (colony size>3000 µm²) in the presence of Epidermal Growth Factor (EGF) (2.5 ng/ml). The maximal response of the assay is about 2500 colonies (>3000 µm²) per dish.

Mitogen Assay:

NRK-fibroblasts were suspended in medium (Dulbecco's Modified Eagles Medium supplemented with 100 units per ml penicillin and 100 µg per ml streptomycin), 10% in calf serum. Cells ($4\times10^3$ in 0.1 ml) were seeded in 96-well microtitre plates and incubated overnight. (All incubations proceeded at 37° C. in a humidified atmosphere of 10% $CO_2$ in air). The resulting monolayers were washed twice with 0.2-ml portions of serum-free medium and once with 0.2 ml of medium containing 0.2% calf serum. DME, 0.2% in calf serum (100 µl), was added to the washed monolayers. The cells were incubated for 3–4 days during which time they reached about 75% confluency. Test samples (50 µl, freeze-dried from 1M acetic acid and redissolved in 20 µl of sterile 4 mM HCl and 40 µl of serum-free medium) were added to the growth arrested cells. After incubation (17 h), $^3$H-thymidine (80 Ci/mmol) was added (1 µCi in 50 µl of serum-free medium). Four hours later the medium was removed, and the cells were fixed (10 min at 4° C.) with ice-cold 5% trichloroacetic acid (0.2 ml). Fixed cells were washed 4 times with 0.2-ml portions of 5% trichloroacetic acid. Precipitated radioactivity was solubilized by incubation in 0.5M NaOH (0.15 ml per well for 30 min at 37° C.).

RESULTS AND INTERPRETATION

The biological properties of purified, platelet-derived TGF-β are shown below in Table 4. In the presence of EGF, the TGF elicits near maximal transforming activity at a concentration of 1 ng/ml. In agreement with the data of others using impure TGF-β, the activity of the growth factor is destroyed by reduction; stimulation of colony formation by an EGF/reduced TGF-β mixture was no greater than the EGF alone. Moreover, TGF-β, assayed in the absence of EGF, gave the basal level (shown by 10% calf serum) of transforming activity. Other experiments showed that TGF-β (1 ng/ml) does not compete for the binding of $^{125}$I-labeled EGF to the EGF receptor.

TGF-β can be detected in the platelet extract at protein concentrations showing no mitogenic activity. Table 4 shows that purified TGF-β (1 ng/ml) does not stimulate $^3$H-thymidine incorporation into NRK-fibroblasts despite the fact that these cells respond to established mitogens. [Decreased $^3$H-thymidine incorporation, relative to basal, was observed with TGF-β when used at concentrations greater than 0.1 ng/ml. At no concentration tested (0.01–10 ng/ml) did the TGF stimulate $^3$H-thymidine incorporation]. In addition to confirming that platelet-derived TGF-β is biologically distinct from PDGF, these data suggest that the role of TGF-β in inducing cell growth in soft agar may be unrelated to a direct stimulation of total DNA synthesis.

The sensitivity of TGF-β to treatment with dithiothreitol (Table 4) indicates that disulfide bonds likely play an important role in conferring structure to the molecule. The molecular weight of platelet-derived TGF-β, as determined by SDS-polyacrylamide gel electrophoresis, is affected by treatment with reductant. This result indicates that the native protein ($M_r$=25,000) is composed of two polypeptide chains of very similar molecular weight ($M_r$=12,500) which are maintained in covalent association by disulfide bonds. (The inability to detect contaminants in the presence as well as absence of reductant further confirms the purity of the protein).

TABLE 4

Biological effects of purified platelet-derived TGF-β

| Sample | Number of Colonies (>3000 µm²) | Amount of $^3$H-Thymidine Incorporation (CPM) |
| --- | --- | --- |
| TGF-β & EGF | 1980 | ND |
| reduced TGF-β & EGF | 380 | ND |
| EGF | 400 | 45,200 |
| TGF-β | 25 | 4,800 |
| calf serum (10%) | 12 | 86,000 |

This table shows the biological properties of purified TGF-β at a concentration of 1 ng/ml (a concentration 10-fold greater than that yielding 50% of maximal transforming activity). EGF was used at 2.5 ng/ml, its concentration in the TGF-β bioassay. The growth factors were dissolved in 1M acetic acid with 10 µg BSA as carrier and freeze-dried prior to analysis. To prepare reduced TGF-β, the lyophilized growth factor and BSA carrier were treated with a molar excess of dithiothreitol (0.05M in 0.2 ml of 0.1M sodium phosphate buffer, pH 7.4; 3 h at 37° C.). The solution of reduced TGF-β was acidified with acetic acid (40 µl), dialyzed against 1M acetic acid in a microdialysis unit, and freeze-dried prior to analysis. EGF was added to the sample after dialysis. A mock reduction (performed in the absence of dithiothreitol) had no effect on TGF-β transforming activity. In the mitogen assay, the basal level of $^3$H-thymidine incorporation (determined in the absence of mitogen) was 9000–10,000 CPM. The mitogenic activity of TGF-β was not determined (ND) in the presence of EGF.

TABLE 5

Partial Amino Acid Sequence of Platelet-derived TGF-β

5
Ala—Leu—Asp—Thr—Asn—Tyr—X—Phe—Ser (where X is undetermined) as determined by Edman Degradation, each subunit probably having the same above sequence.

EXAMPLE 7

TGF-β From Human Placenta Ser. No. 06/500,927)

The acid-ethanol extract of human placenta displayed activity that stimulated anchorage-dependent NRK cells to form colonies in soft agar. EGF markedly enhanced (150 fold) the activity of this placental TGF. As has been previously demonstrated for other TGFs, the activity of a partially purified placental preparation was destroyed by treatment with either trypsin or dithiothreitol.

Chromatography of the undialyzed crude residue from the combined acid-ethanol extractions of 11 placentas on a column in 1M acetic acid gave two peaks of activity when assayed in the presence of EGF (pool A, apparent $M_r$ 5000–9000 and pool C, apparent $M_r$ less than 3500). No colony stimulating activity was detected when equivalent aliquots were assayed in the absence of EGF. Therefore, all subsequent soft agar assays were performed in the presence of 2 ng/ml EGF. None of the 3 pools competed with $^{125}$I-EGF for EGF membrane receptor sites on CCL-64 cells. This placenta-derived TGF is therefore clearly a member of the TGF-β family. Pool A, which contained 47% of the recovered protein, had 17% of the recovered TGF activity (see Table 6) while pool C, with only 3.3% of the protein, contained 18% of the recovered activity. Pool B did not give a valid assay for TGF activity because of the presence of a growth inhibitory substance. This inhibitor could be separated from the soft agar colony forming activity by further chromatography. As indicated in Table 6, 69% of the TGF activity found in the crude residue was present in the pool B fraction that eluted from the column. Pools B and C were therefore used for further purification.

Application of the protein from the gel filtration column to a cation-exchange column and subsequent elution of the applied material with a linear sodium chloride gradient, gave a single peak of soft agar colony forming activity. Although 85–96% of the applied protein was recovered from the column, only 10–45% of the applied TGF activity was detected. Whether this loss of activity is due to specific loss of the TGF protein, to denaturation of the TGF, or to the separation of the TGF from an activator is, at this time, still under investigation. Fractions were pooled and chromatographed on HPLC column using an acetonitrile-0.1% TFA gradient. The TGF activity for both pools eluted from the column as a single peak at an acetonitrile concentration of 35%. Rechromatography of this material on a CN support equilibrated in n-propanol-0.1% TFA yielded a single peak of TGF activity at 35% n-propanol which corresponded to a strong absorbance peak. The homogeneity of the final preparation was indicated by gel electrophoresis. The final degree of purification of placenta derived TGF-β from the crude extract was 110,000–124,000 fold with a 1.1% recovery of activity in pool C and 4.8% in pool B. Only 64–72 pg/ml of placental TGF-β was needed to obtain a half-maximal growth stimulatory response ($ED_{50}$) in the presence of 2 ng/ml of EGF.

The purity of the final TGF preparation was also demonstrated by $NaDodSO_4$-polyacrylamide gradient gel electrophoresis. In the absence of β-mercaptoethanol, a single polypeptide band with an apparent molecular weight of 23,000–25,000 was observed for TGF from either pool B or pool C. Reduction of the protein with β-mercaptoethanol produced a single band at approximately 13,000 molecular weight. When the gel was sliced into 0.5 cm strips and the unreduced protein eluted into 1M acetic acid, all the TGF activity was found in the slice that corresponded to a molecular weight of 23,000–25,000, clearly indicating that the TGF activity corresponded to the only detectable protein band.

Examples of Extraction, Purification, and Analysis

Soft Agar Assay

Soft agar colony forming activity was determined as described previously except that the cells were stained at the end of one week in assay and the number and size of the colonies were determined using image analysis system.

Extraction

Normal term human placentas were frozen on dry ice within 30 minutes after delivery and stored at −60° C. until used. Placentas were extracted using a procedure previously described in Roberts et al, Proc. Nat. Acad. Sci. USA, 77:3494–3498 (1980), except that the homogenized tissue (600–1000 g) was stirred in the acid-ethanol solution at room temperature for 2 to 3 hrs prior to centrifugation. The resulting supernatant was adjusted to pH 3.0 and protein precipitated with ether and ethanol. The precipitate was collected by filtration and redissolved in 1M acetic acid (1 ml/g of tissue). Insoluble material was removed by centrifugation, the supernatant lyophilized and the residue (27 mg per gram wet weight placenta) stored at −20° C.

Gel filtration chromatography

The lyophilized extract (239 g) from 11 placentas (8.8 kg) was redissolved in 1M acetic acid (50 mg residue per ml) and applied in two separate portions (107 g and 132 g residue) to a column (35.6×90 cm) containing acrylamide gel (100–200 mesh), equilibrated and eluted (1.6 L/hr) with 1M acetic acid at room temperature. Fractions (800 ml) were collected and aliquots of the even numbered fractions were assayed for protein and for growth promoting activity in soft agar. The fractions containing TGF activity were combined into three separate pools (A–C) and lyophilized. Pool B (6 g residue per column) was redissolved in 1M acetic acid (60 mg/ml) and applied to a column (10×91 cm) containing P-6 acrylamide gel equilibrated with 1M acetic acid. The protein was eluted from the column with 1M acetic acid (150 ml/hr), collecting 37 ml fractions. Aliquots of even numbered fractions were assayed for TGF activity. The fractions containing this activity were pooled and lyophilized.

Ion-Exchange Chromatograph

Twenty-four percent of pool B from the P-6 column (2.1 g protein) and pool C from the P-30 column (1.9 g protein) were redissolved separately in 60 ml 0.01M acetic acid. The pH was adjusted to 4.5 and the conductivity to 1.2–1.5 mS/cm. Each sample was then applied to a cation exchange column (CM-Trisacryl M, LKB, 5×10 cm) equilibrated in 0.05M sodium acetate, pH 4.5 (buffer A). The column was eluted with 300 ml of buffer A (145 ml/hr) followed by a linear sodium chloride gradient to 0.70M sodium chloride in buffer A at 0.8 mM/min. After 70 fractions (29 ml/fraction), the column was washed with 1M sodium chloride, 0.05M sodium acetate, pH 2.5 and then reequilibrated with buffer A. Aliquots from the even numbered fractions were removed for determination of protein and TGF activity. The peak of activity was combined for further analysis.

Reverse-Phase HPLC

The sample from the ion-exchange column was made 10% (v/v) in acetonitrile, 0.1% (v/v) in trifluoroacetic acid (TFA) and the pH adjusted to 2.0, It was then pumped onto an HPLC column (10 μm particle size, 0.78×30 cm) equilibrated in acetonitrile:water:TFA (10:90:0.1), two polypeptide chains of very similar molecular pH 2. After washing the sample onto the column with 50 ml of the initial solvent, the column was eluted (1.2. ml/min) with a 60 min linear gradient from 25:75:0.1 to 45:55:0.1 acetonitrile:water:TFA, pH 2. After 75 fractions (1.2 ml/fraction) the column was stripped with acetonitrile:water:TFA (80:20:0.1), pH 2, collecting 2.4 ml fractions. Aliquots (5 μl) were removed for assay of TGF activity.

The peak of TGF activity from the HPLC column was combined, lyophilized, redissolved in n-propanol: water:TFA (30:70:0.1), pH 2, and applied to a CN column (10 μm particle size, 0.38×30 cm) equilibrated with the sample solvent. The column was then eluted (1.1 ml/min) with a 153 min linear gradient from 30:70:0.1 to 45:55:0.1 n-propanol:water:TFA, pH 2. Forty-five fractions (2.2 ml/fraction) were collected and aliquots were removed for bioassay, amino acid analysis, and gel electrophoresis.

$NaDodSO_4$-Polyacrylamide Gel Electrophoresis

Samples were analyzed on 1.5 mm slab gels using either a polyacrylamide gradient of 15 to 28% or a 15% polyacrylamide gel and a discontinuous buffer system. Proteins were fixed with formaldehyde and stained using a silver staining technique. In some cases, samples were boiled with 5% β-mercaptoethanol for 3 min prior to application to the gel.

Other procedures

Total protein was determined either by the dye-binding method or fluorescamine assay using bovine serum albumin as standard or by amino acid analysis. Assays for EGF-competing activity were performed as previously described.

A summary of a general extraction procedure found to be preferable to previously used procedures, is given below.

Example of a Placenta Derived TGF-β Extraction Protocol

1. Placentas are placed on dry ice immediately after delivery and are stored at −70° C. or colder until used.
2. Approximately 24 hr before extraction, thaw placentas at −20° C.
3. Chop 1 kg of placenta into pieces and place into extraction solution (4 L solution/kg tissue).
   Extraction Solution:
   3189 ml 95% ethanol
   770 ml water
   66 ml concentrated HCl
   210 mg phenylmethylsulfonyl fluoride
   12 mg pepstatin A
4. Mince in a blender to give a slurry.
5. Stir slurry at room temperature for approximately 2½ hr (requires heavy-duty stirrer).
6. Centrifuge—17,700×g—10 min.; Discard pellet, save supernatant.
7. Adjust the supernatant to pH 3.0 with concentrated ammonium hydroxide.
8. Add 0.55 volume to 5.5M NaCl.
9. Precipitate overnight at 4° C.
10. Centrifuge—17,700×g—10 min. Discard pellet, save supernatant.
11. Concentrate supernatant to ⅕ volume or less. (We used a hollow fiber concentrator with a 5000 MW nominal cutoff membrane).
12. Add 2 volumes 5.5M NaCl to concentrated supernatant.
13. Precipitate overnight at 4° C.
14. Centrifuge—17,700×g—10 min. Discard supernatant. Save pellet for gel filtration chromatography and further purification.

TABLE 6

Purification of TGF-β from human placenta.

| Purification step | Protein* recovered (mg) | $ED_{50+}$ (ng/ml) | Specific++ activity (units/ug) | Total activity (units × $10^3$) | Degree of purification (fold) | Recovery of activity (%) |
|---|---|---|---|---|---|---|
| 1. Crude Extract | 239,000 | 7,600 | 0.09 | 21,510 | 1.0 | 100 |
| 2. Acrylamide Gel #1 | | | | | | |
| Pool A | 73,900 | 15,000 | 0.05 | 3,695 | 0.6 | 17 |
| Pool B | 27,720 | — | — | — | — | — |
| Pool C | 1,900 | 360 | 2.0 | 3,800 | 22 | 18 |
| 3. Acrylamide Gel #2 Pool B | 8,700 | 410 | 1.7 | 14,790 | 19 | 69 |
| 4. Ion-Exchange | | | | | | |
| Pool B§ | 140 | 62 | 11.5 | 1,610 | 128 | 31 |
| Pool C | 46.3 | 85 | 8.4 | 390 | 93 | 1.8 |
| 5. HPLC—$C_{18}$ | | | | | | |
| Pool B | 0.27 | 0.10 | 7,000 | 1,900 | 77,000 | 37 |
| Pool C | 0.26 | 1.2 | 595 | 155 | 6,610 | 0.7 |
| 6. HPLC—CN | | | | | | |
| Pool B | 0.025 | 0.072 | 9,920 | 248 | 110,000 | 4.8 |
| Pool C | 0.022 | 0.064 | 11,160 | 245 | 124,000 | 1.1 |

*For steps 1 to 4, total protein was determined by the dye-binding procedure (15). For steps 5 and 6, total protein was based on amino acid analysis.
+$ED_{50}$ is defined as the concentration (ng/ml) of TGF-β required to give a response of 1 unit in the presence of EGF (1 unit of activity gives 50% maximal response, approximately 1000 colonies >3000 μm$^2$ plate).
++ Specific activity = $\frac{1 \text{ unit}}{ED_{50} \text{ (total ml per petri dish)}} \times 1000$
§Twenty-four percent of pool B from step 3 was used for further purification.

Table 6, above, summarizes the examples and results of the purification.

TABLE 7

Partial Amino Acid Sequence For Each Of The Two Human Placenta TGF-β subunits.
(CMC is half-cystine or cysteine, determined as S-carboxymethylcysteine).

```
                 5                    10
Ala—Leu—Asp—Thr—Asn—Tyr—CMC—Phe—Ser—Ser—
                 15                   20
Thr—Glu—Lys—Asn—CMC—CMC—Val—X—Gln—Leu—
                 25           29
Tyr—Ile—Asp—Phe—X—Lys—Asp—Leu—Gly—
``` where X is undetermined.

Summary and Discussion of Results

A TGF has been isolated from the acid-ethanol extract of human placenta. It is classified as a type β TGF, because it does not compete with EGF for membrane receptor sites but requires EGF for the induction of colony growth in soft agar, with a 50% maximal formation of colonies greater than 60 μm diameter occurring at 64–72 pg TGF per ml ($3 \times 10^{-12}$M). The factor has been purified to homogeneity by gel filtration, cation-exchange and high-pressure liquid chromatography. It is a protein of molecular weight 23,000 to 25,000 and is composed of two polypeptide chains of approximately 13,000 molecular weight held together by disulfide linkages. Whether these chains are identical or different remains to be determined. Although the protein contains 16 half-cystine residues, it is not yet known whether all of these residues are involved in disulfide linkage. However, the extreme stability of the TGFs to acid treatment and heat denaturation suggests the presence of a large number of such bonds.

The presence of TGFs in the crude acid-ethanol extract of human placenta that were able to compete with EGF for binding to membrane receptors (TGF-αs) has recently been noted in Stromberg et al, Biochem. Biophys. Res. Commun., 106:354–361 (1982). In the present invention, a significant amount of TGF-α-like activity was not detected. Although some soft agar colony forming activity was found in the crude residue in the absence of EGF, this activity did not compete with EGF in a receptor binding assay and it was stimulated 150 fold by the addition of 2 ng/ml of EGF, indicating that most, if not all, of the TGF present was of the type β class. Also, as the placental TGF was purified, it became totally dependent on exogenous EGF for soft agar colony forming activity. Part of this difference may be explained by the fact that in Stromberg et al (1982) colonies of 6 cells or greater were considered to be significant while for the present invention colonies had to contain at least 60 cells in order to be counted.

A TGF-β at a concentration of 430 ng per gram wet weight of tissue has recently been purified from human platelets. Because placenta contains much blood, it is possible that the placental TGF-β (10 ng per gram of tissue) originated from the platelets. However, even assuming that the placenta was 100% blood and that platelets comprised 0.2% of this blood, platelet TGF would account for only 8% of the recovered placental TGF. Therefore, if the placental TGF β did originate from the platelets, it would have to be concentrated by an, as yet, unknown mechanism.

Blood platelets also contain the peptide, platelet derived growth factor (PDGF). However, placental TGF-β is not PDGF, as clearly demonstrated by the results from two different assays. In the first assay, placental TGF-β did not have any chemotactic activity when tested under conditions where PDGF displayed strong activity. Similarly, placental TGF-β did not compete with PDGF in a radioreceptor assay.

Although TGFs were originally found in tumor cells and were postulated to be involved in transformation and neoplastic cell growth, their presence in adult cells and tissues, in platelets, and in embryos [as reported in Twardzik et al, Cancer Res., 42:590–593 (1982)] imply that TGFs have a normal physiological function as well. The purification of placental TGF-β to homogeneity facilitates investigation of this function, since it permits the development of both receptor binding and radioimmunoassays. These assays not only allow a specific, quick procedure for quantitation of TGF-β but will also permit investigation of the mechanisms of action and the control of expression of TGF-βs under normal and neoplastic conditions. Finally, structural analysis of purified TGF-β provides information for initiation of cloning experiments. This will allow eventual production of large quantities of human TGF-β, which might have useful therapeutic applications in enhancement of wound healing and tissue repair.

What is claimed is:

1. A method for promoting cell proliferation in mammals which comprises applying to a mammal in need of such treatment an effective amount of beta-transforming growth factor (TGF-β) having the following characteristics;
    (a) does not compete with epidermal growth factor (EGF) for receptor binding;
    (b) induces dose dependent formation of large colonies having a size of greater than 3,100 μm² of NRK 49F cells in a soft agar assay when activated by EGF or transforming growth factor-alpha (TGF-α) and
    (c) if not activated by EGF or transforming growth factor-alpha, does not induce NRK cells to form said large colonies in soft agar.

2. The method of claim 1, wherein said TGF-β is applied topically.

3. The method of claim 1, wherein said TGF-β is applied systemically.

4. A method for promoting cell proliferation in mammals which comprises applying to a mammal in need of such treatment an effective amount of a composition comprising:
    an effective cell proliferation enhancing amount of isolated and substantially homogeneous beta transforming growth factor (TGF-β) having the following characteristics:
    (a) acid stable;
    (b) an apparent molecular weight of about 25,000 to 26,000 daltons in the absence of a reducing agent as measured by SDS-PAGE;
    (c) an apparent molecular weight of about 12,500 daltons under reducing conditions as measured by SDS-PAGE;
    (d) does not compete with epidermal growth factor for receptor binding;
    (e) induces dose-dependent formation of large colonies having a size of greater than 3,100 μm² of NRK 49F cells in a soft agar assay when activated by epidermal growth factor (EGF) or transforming growth factor-alpha (TGF-α); and being purified to the extent that
        (1) it does not itself induce NRK cells to form said large colonies in soft agar and
        (2) a single band with an apparent molecular weight of about 12,500 daltons is shown on SDS-PAGE under reducing conditions and a single band with an apparent molecular weight of about 25,000 is shown under non-reducing conditions; and a pharmaceutically acceptable carrier therefor.

5. A method of promoting proliferation of cells in an animal comprising:
    administering to the animal a composition comprising a TGF-beta activating agent, a pharmaceutically acceptable carrier, and a polypeptide that (a) is active in the TGF-beta assay, (b) is a dimer having an approximate molecular weight of about 25,000–26,000 daltons as determined by SDS-PAGE, and (c) is purified, wherein said polypeptide and activating agent are present in amounts sufficient to promote cell proliferation.

6. The method of claim 5, wherein each chain of said dimer has the following N-terminal sequence: Ala-Leu-Asp-Thr-Asn-Tyr-CMC-Phe-Ser-(Ser)-Thr-Glu-Lys-Asn-CMC wherein CMC is S-carboxymethylcysteine.

* * * * *